US005759540A

United States Patent [19]

Nielsen

[11] Patent Number: 5,759,540
[45] Date of Patent: Jun. 2, 1998

[54] METHOD AND CASE FOR DISINFECTION OF CONTACT LENSES

[76] Inventor: Tom Buris Nielsen, Taalforvej 16, DK-8250 Egaa, Denmark

[21] Appl. No.: 362,527

[22] PCT Filed: Jun. 28, 1993

[86] PCT No.: PCT/DK93/00211

§ 371 Date: Mar. 29, 1995

§ 102(e) Date: Mar. 29, 1995

[87] PCT Pub. No.: WO94/01800

PCT Pub. Date: Jan. 20, 1994

[30] Foreign Application Priority Data

Jul. 6, 1992 [DK] Denmark ................. 0885/92

[51] Int. Cl.$^6$ .............. A61K 38/44; A61K 9/14; C12N 11/00

[52] U.S. Cl. .............. 424/94.4; 134/10; 134/26; 134/104.1; 134/201; 134/901; 252/186.28; 422/30; 422/292; 424/484; 424/616; 435/174; 435/262; 435/264; 435/288; 504/186.31

[58] Field of Search ............... 252/186.28; 504/186.31; 424/94.4, 484, 616; 435/174, 262, 264, 288.1, 975; 134/10, 26, 104.1, 201, 901; 422/30, 292

[56] References Cited

U.S. PATENT DOCUMENTS

| | | | |
|---|---|---|---|
| 4,011,941 | 3/1977 | Parsons | 206/5.1 |
| 4,826,658 | 5/1989 | Kay | 422/30 |
| 4,860,885 | 8/1989 | Kaufman et al. | 206/5.1 |
| 5,011,661 | 4/1991 | Schäfer et al. | 422/30 |
| 5,088,146 | 2/1992 | Smith et al. | 15/104.94 |
| 5,384,091 | 1/1995 | Rontome et al. | 422/30 |
| 5,491,091 | 2/1996 | Loshaek et al. | 436/1 |
| 5,531,963 | 7/1996 | Powell, Jr. | 422/30 |
| 5,556,480 | 9/1996 | Rontome et al. | 134/26 |

Primary Examiner—David M. Naff
Assistant Examiner—Deborah K. Ware
Attorney, Agent, or Firm—Antonelli, Terry, Stout, & Kraus, LLP

[57] ABSTRACT

A method and case for disinfection of contact lenses wherein the contact lenses are placed in a double chamber filled with cleaning fluid, for example, hydrogen peroxide, with the case comprising a third chamber or position connected with the double chamber. The third chamber is adapted to take up and hold a tablet containing a neutralization agent such as catalase, so that the hydrogen peroxide in the double chamber is neutralized suitably slowly by admission of the cleaning fluid to dissolve the tablet. By the dissolution of the tablet, oxygen is generated, and an oxygen bubble is formed around the tablet so that the hydrogen peroxide is alternately kept from the tablet and ultimately is admitted access to the tablet. Rather than provide a double chamber, a holder member may be provided for holding the respective contact lenses, with the tablet being accommodated at a lower end of the holder and being exposed to the cleaning fluid when the holder is inserted into the cleaning fluid.

14 Claims, 3 Drawing Sheets

METHOD AND CASE FOR DISINFECTION OF CONTACT LENSES

FIELD OF THE INVENTION

The present invention relates to a method and case for disinfection of contact lenses wherein the contact lenses are placed in a hydrogen peroxide solution, in a case, and where neutralization of the cleaning fluid is carried out over a period of time by a NaCl tablet containing a neutralization agent catalyst, or the NaCl is slowly dissolved during the neutralization process.

BACKGROUND OF THE INVENTION

Users of contact lenses, particularly soft contact lenses, are familiar with the fact that contact lenses frequently, preferably daily, have to be cleaned to avoid inconveniences in the use of contact lenses.

Normally hydrogen peroxide is used for disinfection of contact lenses which are placed in special cases, which may be used for the storage of the contact lenses as well as for disinfection of the lenses. The contact lenses are kept in the cleaning fluid (hydrogen peroxide) until their next use, for example through the night.

In order to neutralize the hydrogen peroxide before next use of the contact lenses, it is known to neutralize the hydrogen peroxide with a "platinum star", which acts as a catalyst, or using an enzyme tablet containing, for example catalase, to neutralize the hydrogen peroxide.

U.S. Pat. No. 4,011,941 discloses an apparatus comprising a cleaning capsule for sterilizing soft contact lenses in an aqueous hydrogen peroxide solution and a method where the neutralizing agent is brought into contact with the cleaning solution by inverting the cleaning capsule—and where use is made of a catalytic reactor coated with a layer of platinum.

To ensure that there will be time enough for the hydrogen peroxide to disinfect the contact lenses from microorganisms and viruses before the neutralization, it is furthermore known to delay the effect of catalase using a special tablet, where the catalase is coated with methyl-cellulose or a PVP-film. EP-A-O 209 071 discloses the use of such an encapsulated neutralizing tablet which is inserted into the cleaning solution and releases the neutralizing agent with delay.

Catalase is an enzyme, which is capable of converting the hydrogen peroxide into water and free oxygen. In practice, the tablet used contains a salt with catalase, so that the hydrogen peroxide is converted into physiological salt water.

SUMMARY OF THE INVENTION

The purpose of the invention is to provide a method enabling a further improvement in disinfection of contact lenses.

The method according to the invention is distinctive in that disinfection of the contact lenses and neutralization of the cleaning fluid, respectively, are controlled by a tablet which is not coated and contains the enzyme catalase, said tablet is placed in a separate chamber or in a special position, and that the admission of a cleaning fluid to this chamber or this position is controlled by the generation of oxygen by the reaction between the cleaning fluid and the enzyme catalase.

In a simple manner it hereby becomes possible to control the duration of the disinfection as well as the neutralization of the cleaning fluid with a simple catalase tablet, which does not need any coating, that is a rather cheap catalase tablet may be used to control of a slowly, delayed neutralization of the cleaning fluid.

The invention furthermore relates to a case for use in carrying out the method according to the invention, which case is distinctive in that it comprises a chamber with a room for a right contact lens and a room for a left contact lens, and a chamber or a special position, which is adapted to receive a catalase tablet, said chambers are connected with each other in such a manner that the admission of the cleaning fluid to the neutralization agent is controlled.

Expediently, the case is provided with an opening between said chamber for the contact lenses and said chamber for the catalase tablet, said opening for free access of fluid is placed in a level just under the tablet in the chamber, the position of said opening is adapted to control the speed of the neutralization by controlling the oxygen stream from said chamber or said special position, respectively to the chamber for the contact lenses.

BRIEF DESCRIPTION OF THE DRAWINGS

The invention is described in the following with reference to the drawing, in which.

DETAILED DESCRIPTION

Figure 1:
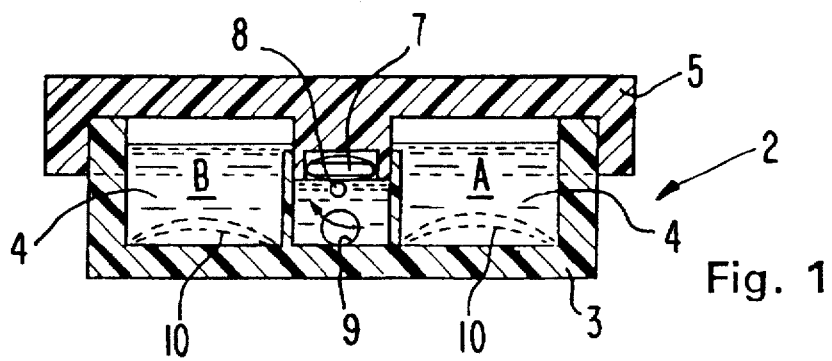
FIG. 1 shows a sectional view through a preferred embodiment for a case according to the invention, shown with contact between tablet and cleaning fluid.
Figure 2:
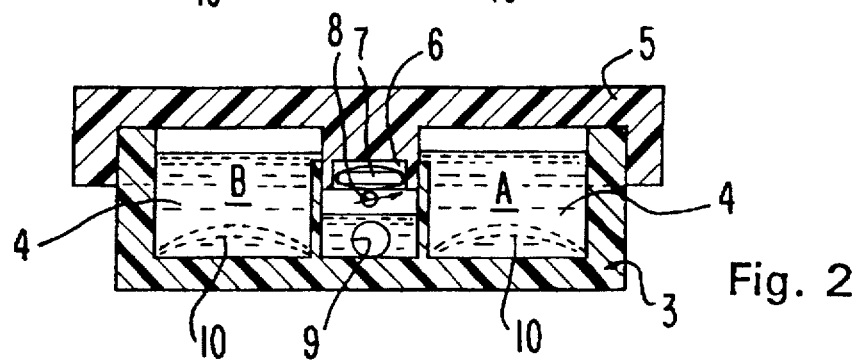
FIG. 2 shows a similar sectional view as FIG. 1, but shown in a situation, where the cleaning fluid, because of the oxygen generation, is forced away from the tablet.
Figure 3:
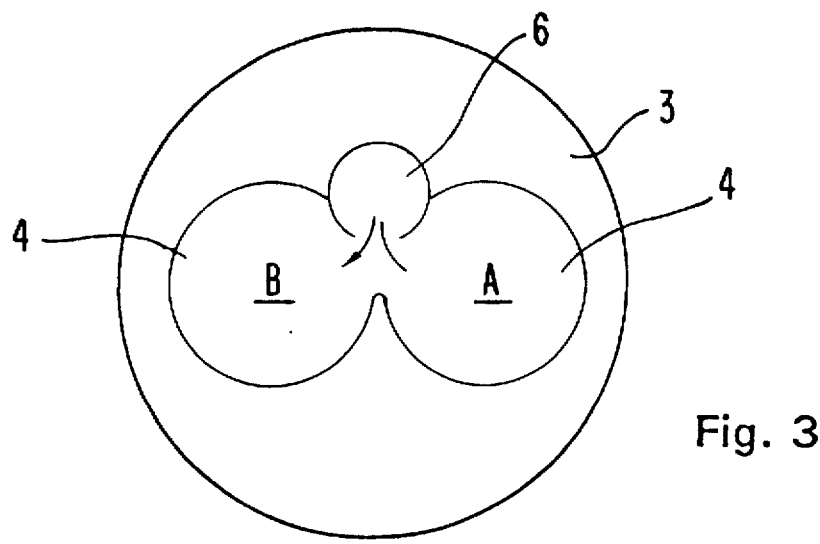
FIG. 3 shows the case, as seen from above and without a lid part.

A case 2, shown in FIGS. 1–3, consists of a case part 3 having a chamber with a room A to accommodate a right contact lens and a room B to accommodate a left contact lens and a lid part 5 (FIG. 4) with a chamber 6 or a special position adapted to keep or fix a tablet 7 containing catalase or another enzyme.

A pair of contact lenses 10 to be cleaned or disinfected is placed in the double chamber 4, and cleaning fluid in the form of hydrogen peroxide (FIG. 1) is added. A catalase tablet 7 is squeezed in the chamber 6, or the special position of the lid part. The chamber 6 has for that purpose a projecting, lower edge 11, behind which the tablet 7 is squeezed, before the lid part 5 is again placed on the lower part 3.

Contact between the catalase tablet 7 and the hydrogen peroxide generates free oxygen, and an oxygen bubble (FIG. 2) is formed around respectively under the tablet 7, so that the generation of oxygen is reduced. In the side of the chamber 6 an opening 8 is provided into the double chamber 4, through which opening 8 the oxygen bubble may escape. Afterwards the hydrogen peroxide is readmitted to the catalase tablet 7, and a new portion of oxygen is generated and escapes through the opening 8 or escapes otherwise with this procedure continuing until the tablet 7 is dissolved.

Eventually the lower case part 3 on level with the chamber 6 in the lid part 5 may comprise a complementary part, which is provided with a side opening 9 in order to improve the circulation between the rooms A, B of the double chamber around the contact lenses 10 (FIGS. 1 and 2).

Figure 4:
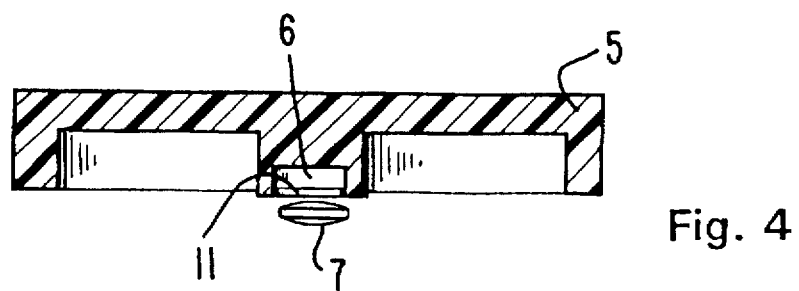
FIG. 4 shows a side sectional view of a lid part with a holding cavity for the neutralization tablet.
Figure 5:
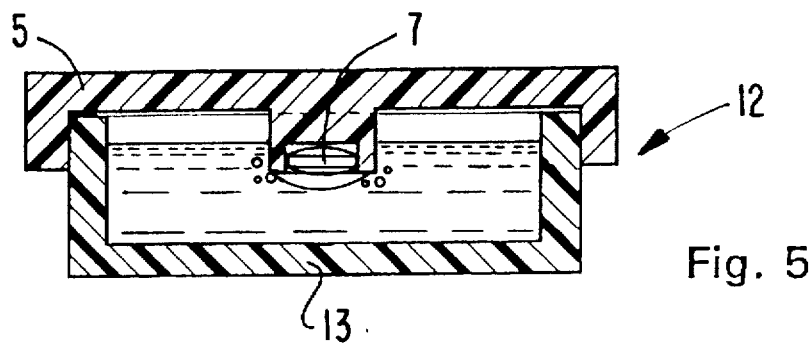
FIG. 5 shows a sectional view through another embodiment for a case according to the invention, shown in a position, where an oxygen bubble maintains the cleaning fluid away from the tablet.
Figure 6:
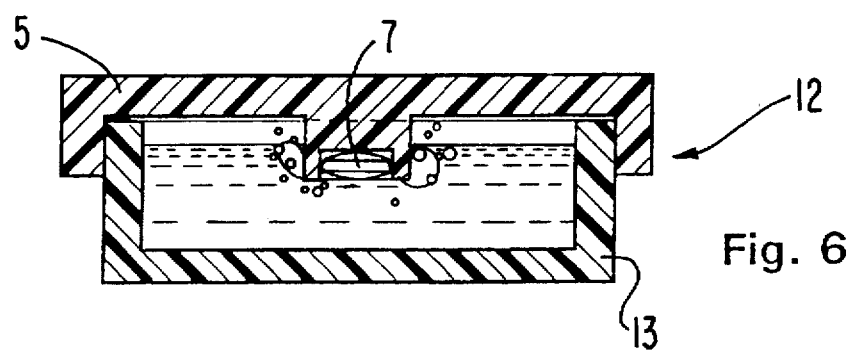
FIG. 6 shows a similar sectional view as FIG. 5, but shown in a situation, where the oxygen bubble is escaping and permits access of fresh cleaning fluid to the tablet.
Figure 7:
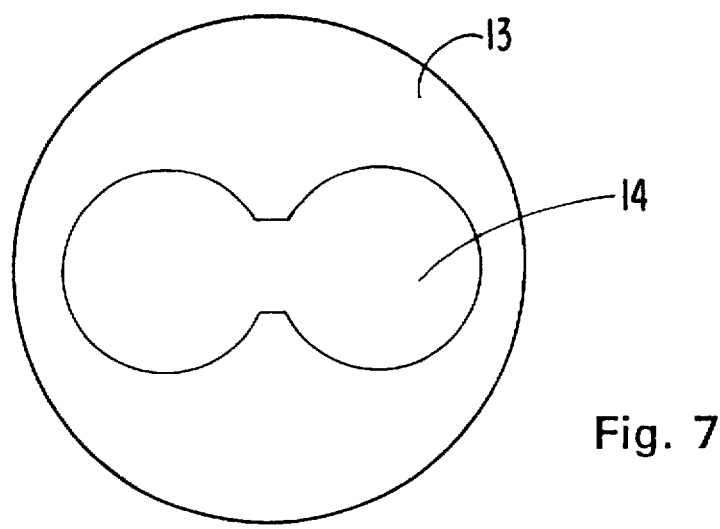
FIG. 7 shows the case as in FIGS. 5 and 6 as seen from above and without a lid part.

Another embodiment of a case 12 according to the invention shown in FIGS. 5–7 comprises a lower case part 13 having a double chamber 14 with two positions to accommodate a pair of soft contact lenses and a lid part 5 with a similar configuration as that of the lid part 5 shown in FIG. 4.

Figure 8:
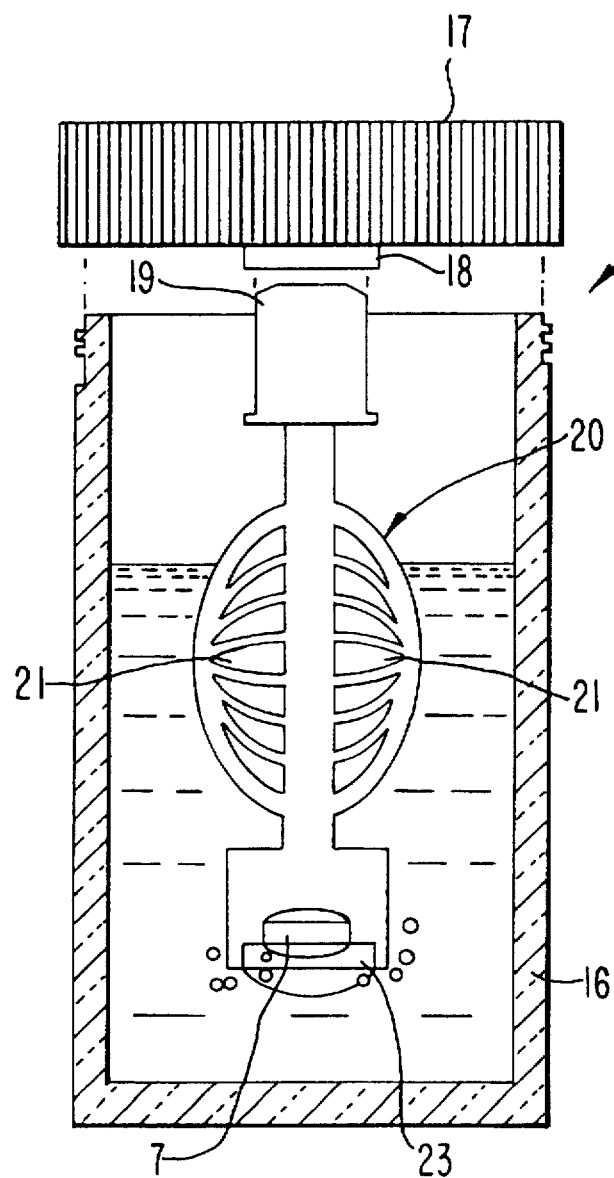
FIG. 8 shows an end view of a prior art case for keeping and cleaning contact lenses and provided with a combined lens and tablet holder using the method according to the invention.
Figure 9:
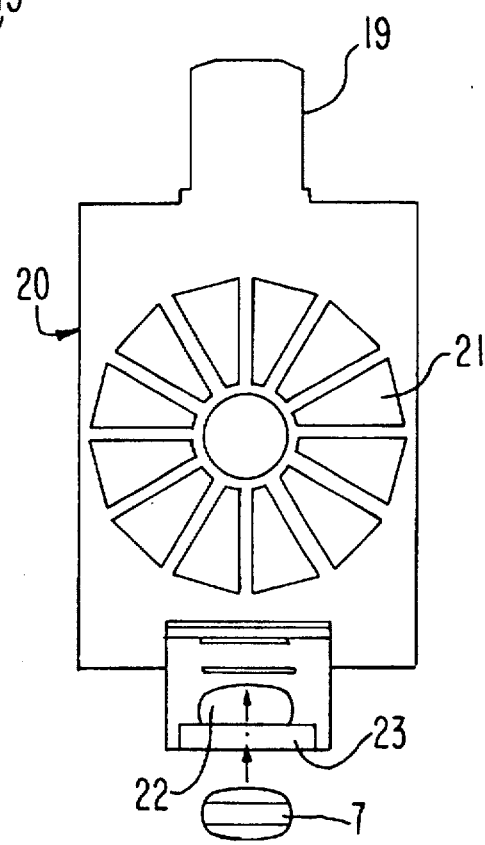
FIG. 9 shows a side view of the combined lens and tablet holder of FIG. 8.

In FIG. 8 is shown a known case 15 comprising a lower case part 16 and a threaded lid 17 with a central socket 18, accommodating a top end portion 19 of a holding member 20 with two basket like chambers 21 adapted to keep a pair of contact lenses as the holding member 20 is submerged into a cleaning fluid. At the bottom end of the holding member 20 a special cavity 22 or position is provided with a collar 23 adapted to receive and fix a catalase tablet 7. The holding member 20 is shown from the side in FIG. 9.

I claim:

1. A method for disinfecting contact lenses, the method comprising the steps of:

placing the contact lenses in a cleaning fluid contained in a case said cleaning fluid comprising hydrogen peroxide, and controlling a period of time for disinfecting the contact lenses and neutralization of the cleaning fluid by placing a non-coated NaCl-tablet containing a neutralization agent catalase in a separate chamber in the case in such a position that the tablet within the chamber is submerged in the cleaning fluid in the case and admission of the cleaning fluid to the tablet in the separate chamber is delayed by the formation of at least one oxygen bubble generated by a reaction between the cleaning fluid and the catalase, whereby the tablet is slowly dissolved and the cleaning fluid is converted into a pure physiological saline solution.

2. A method according to claim 1, wherein the case contains a lower case part having an open end and containing the cleaning fluid and a lid part for closing the open end of the lower case part, the lid part includes a recessed portion for accommodating the tablet and for defining the separate chamber, and wherein the step of placing of the tablet includes inserting the tablet into the recessed portion of the lid part for accommodating the tablet, and placing the lid part on the lower case part thereby submerging the tablet in the separate chamber within the cleaning fluid.

3. A method according to claim 1, wherein the step of placing of the contact lenses in a cleaning fluid includes mounting the respective contact lenses in a lens holder, and submerging the lens holder with the mounted contact lenses into the cleaning fluid in the case.

4. A method according to claim 1, wherein the step of placing of the contact lenses in a cleaning fluid includes placing the respective contact lenses in two spaced lens accommodating rooms provided in the lower case part of the case.

5. A method according to claim 4, further comprising the step of providing circulation of the cleaning fluid between the two rooms accommodating the respective lenses via an opening between said lens accommodating rooms.

6. A case for enabling disinfection of a pair of contact lenses, the case comprising a lower case part containing a cleaning fluid comprising a hydrogen peroxide solution, a first chamber provided in the lower case part for the contact lenses including a first room for accommodating one of the contact lenses, and a second room spaced from the first room for accommodating the other of the contact lenses, and a lid part for closing an open end of the lower case part, the lid part including a projecting portion having a second chamber for accommodating a non-coated tablet containing a neutralization agent catalase, the tablet being submerged in the cleaning fluid when the lid part is placed on the lower case part and admission of the cleaning fluid to the tablet being delayed by the formation of at least one oxygen bubble generated by the reaction between the cleaning fluid and the catalase within the second chamber, whereby a period of time for disinfecting the contact lenses and neutralization of the cleaning fluid is controlled and the tablet is slowly dissolved, thereby converting the cleaning fluid into a pure physiological saline solution.

7. A case according to claim 6, wherein a further chamber is formed in the lower case part of the case for accommodating the tablet within said second chamber, said further chamber being arranged so that the projecting portion is inserted therein and the tablet is submerged in the cleaning fluid when the lid part is placed on the lower case part.

8. A case according to claim 7, wherein a first opening is provided in a wall of said further chamber which opening communicates with said first chamber formed in the lower case part for enabling a free access of cleaning fluid between the first chamber and said further chamber.

9. A case according to claim 8, wherein a second opening is provided in the wall of said further chamber at a level below the tablet and above said first opening in order to increase the period of time for disinfection and neutralization by controlling a volume of oxygen bubbles escaping through said second opening.

10. A method for disinfecting contact lenses which comprises the steps of placing the contact lenses in a cleaning fluid comprising hydrogen peroxide within a container and effecting neutralization of the cleaning fluid by introducing a non-coated tablet containing a neutralization agent catalase, the step of introducing the tablet comprising positioning the tablet in a separate chamber within said container so that admission of the cleaning fluid into said chamber is delayed by the generation of the at least one oxygen bubble by reaction between the cleaning fluid and the neutralization agent catalase whereby cleaning of the contact lenses and neutralization of the cleaning fluid, respectively, are controlled by dissolution of said tablet in said cleaning fluid.

11. A method according to claim 10, wherein the container comprises a lower case part having an open end and containing the cleaning fluid and a lid part for closing the open end of the lower case part, the lid part including a projecting portion having a chamber for accommodating the tablet and the lower case part having another chamber in which the projecting portion is inserted upon placing the lid part on the lower case part, said projecting portion and said another chamber defining the separate chamber wherein the tablet is positioned and wherein the at least one oxygen bubble is generated by a reaction between the cleaning fluid and the neutralization catalase in said separate chamber and the at least one oxygen bubble acts to control contact of the cleaning fluid with the tablet.

12. A container for disinfecting contact lenses comprising a first chamber containing a cleaning fluid comprising hydrogen peroxide and having a room for a right contact lens and a room for a left contact lens, and a second chamber adapted to receive a non-coated tablet containing a neutralization agent catalase, said first chamber being connected to said second chamber via a first opening and the tablet being positioned in the second chamber in such a manner that admission of the cleaning fluid through said opening into the second chamber is delayed by generation of at least one oxygen bubble by reaction between the cleaning fluid and the neutralization agent catalase.

13. A container according to claim 12, wherein a second opening is provided between said first chamber and said second chamber, said second opening being placed at a level below the position of the tablet in the second chamber and above said first opening, the position of the second opening being adapted to delay the rate of neutralization by delaying discharge of the at least one oxygen bubble from the second chamber.

14. A container according to claim 13, wherein the tablet is positioned at an upper portion of the second chamber.

* * * * *